(12) United States Patent
Young et al.

(10) Patent No.: US 7,670,336 B2
(45) Date of Patent: Mar. 2, 2010

(54) ABLATION PROBE WITH HEAT SINK

(75) Inventors: Kimbolt Young, Newtonville, MA (US); Steve Anderson, Worcester, MA (US); John Spiridigliozzi, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1005 days.

(21) Appl. No.: 11/090,515

(22) Filed: Mar. 25, 2005

(65) Prior Publication Data

US 2006/0217701 A1   Sep. 28, 2006

(51) Int. Cl.
   *A61B 18/14* (2006.01)
(52) U.S. Cl. .......................................................... 606/41
(58) Field of Classification Search ............. 606/27–31, 606/41, 42; 607/96–102
   See application file for complete search history.

(56) References Cited

U.S. PATENT DOCUMENTS

| | | | |
|---|---|---|---|
| 5,273,535 A | | 12/1993 | Edwards et al. |
| 5,417,686 A * | | 5/1995 | Peterson et al. ............... 606/25 |
| 5,545,161 A | | 8/1996 | Imran |
| 5,647,871 A | | 7/1997 | Levine et al. |
| 5,833,688 A * | | 11/1998 | Sieben et al. ................. 606/41 |
| 5,855,576 A | | 1/1999 | LeVeen et al. |
| 5,967,976 A * | | 10/1999 | Larsen et al. ................ 600/374 |
| 6,033,378 A | | 3/2000 | Lundquist et al. |
| 6,287,305 B1 * | | 9/2001 | Heim et al. .................... 606/41 |
| 6,461,351 B1 | | 10/2002 | Woodruff et al. |
| 6,485,455 B1 | | 11/2002 | Thompson et al. |
| 6,595,989 B1 * | | 7/2003 | Schaer ......................... 606/41 |
| 2004/0116793 A1 | | 6/2004 | Taimisto et al. |
| 2004/0181214 A1 * | | 9/2004 | Garabedian et al. ........... 606/41 |
| 2005/0240170 A1 * | | 10/2005 | Zhang et al. ................. 606/27 |

OTHER PUBLICATIONS

PCT International Search Report for PCT/US2006/009051, Applicant: Boston Scientific Scimed, Inc., Form PCT/ISA/210 and 220, dated Aug. 8, 2006 (6 pages).
PCT Written Opinion of the International Search Authority for PCT/US2006/009051, Applicant: Boston Scientific Scimed, Inc., Form PCT/ISA/237, dated Aug. 8, 2006 (6 pages).

* cited by examiner

*Primary Examiner*—Lee S Cohen
(74) *Attorney, Agent, or Firm*—Vista IP Law Group LLP

(57) ABSTRACT

An ablation device includes an electrode having an enclosed lumen, and a heat sink located within the lumen. An ablation device includes an elongated body, an electrode secured to the elongated body, and a heat sink connected to the electrode, wherein the heat sink is confined by the electrode and at least a portion of the elongated body. An ablation device includes an electrode, and a heat sink connected to the electrode, wherein the heat sink is not connected to a pump.

21 Claims, 5 Drawing Sheets

ABLATION PROBE WITH HEAT SINK

FIELD OF THE INVENTION

The field of the invention relates generally to ablation devices for the treatment of tissue, and more particularly, to ablation devices having heat dissipation capabilities.

BACKGROUND

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction. In particular, radio frequency ablation (RFA) may be used to treat patients with tissue anomalies, such as liver anomalies and many primary cancers, such as cancers of the stomach, bowel, pancreas, kidney and lung. RFA treatment involves destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of electrodes (tines) deployable from a cannula. Each of the electrodes includes a proximal end that is coupled to a generator, and a distal end that may project from a distal end of the cannula. The electrodes are arranged in an array with the distal ends located generally radially and uniformly spaced apart from the distal end of the cannula. When using the above described devices in percutaneous interventions, the cannula is generally inserted through a patient's skin, and the tines are deployed out of the distal end of the cannula to penetrate target tissue. The electrodes are then energized to ablate the target tissue. The electrodes may be energized in a bipolar mode (i.e., current flows between closely spaced electrode) or a monopolar mode (i.e., current flows between one or more electrodes and a larger, remotely located common electrode) to heat and necrose tissue within a precisely defined volumetric region of target tissue.

Ablation devices have also been implemented using catheters. Physicians make use of catheters today in medical procedures to gain access into interior regions of the body to ablate targeted tissue areas. For example, in electrophysiological therapy, ablation is used to treat cardiac rhythm disturbances. During these procedures, a physician steers a catheter through a main vein or artery into the interior region of the heart that is to be treated. The physician places an ablating element carried on the catheter near the cardiac tissue that is to be ablated. The physician directs energy from the ablating element to ablate the tissue and form a lesion. Such procedure may be used to treat atrial fibrillation, a condition in the heart in which abnormal electrical signals are generated in the endocardial tissue.

Ablation catheters typically have an elongated shaft carrying an electrode at its distal end. Lesions of different shapes and sizes may be formed by choosing a suitable electrode shape or size, and/or by manipulating the position of the electrode at the distal end of the catheter. An ablation catheter may also have a steering mechanism for steering its distal end, which is beneficial because it allows a physician to steer the catheter through veins and vessel junctions. It also allows the physician to accurately position the electrode carried at the distal end at a target site to be ablated. Steerable ablation catheters have been described in U.S. Pat. Nos. 6,033,378 and 6,485,455 B1, the disclosures of which are expressly incorporated by reference herein.

During use of an ablation device, the electrode delivering ablation energy may overheat, thereby causing tissue charring and preventing formation of a deeper lesion. This may negatively affect the ablation catheter's ability to create a desirable lesion. An overheated electrode may also cause healthy tissue adjacent the target site to be heated. Furthermore, an overheated electrode may cause blood to be heated, thereby creating an undesirable embolism. As such, an ablation device that is capable of cooling an electrode is very desirable.

Ablation devices that have cooling capability are generally connected to a pump via a fluid delivery tube. The pump delivers cooling fluid to the ablation device for cooling an electrode on the ablation device. However, cooling systems that require use of the pump and the fluid delivery tube may be expensive to design and implement, and may be inconvenient and a nuisance to use. For examples, during an operation, the fluid delivery tube connecting the pump and the ablation device may tangle with another medical equipment, or may interfere with the operation. Also, the pump may produce noise that interfere with a physician's concentration, and may disturb conversation between operators in the operation room. In addition, fluid may leak at the pump, at the fluid delivery tube, or at the ablation device. Further, for steerable ablation catheters, if not designed or constructed properly, the fluid delivery tube inside the catheter may kink or buckle during use. For the foregoing reasons, cooling an electrode using fluid delivered from a pump may not be desirable.

Thus, there is currently a need for an improved ablation device that is capable of cooling an electrode during use. Also, it would be desirable that such ablation device does not require use of a pump.

SUMMARY

In accordance with some embodiments, an ablation device includes an electrode having an enclosed lumen, and a heat sink located within the lumen.

In accordance with other embodiments, an ablation device includes an elongated body, an electrode secured to the elongated body, and a heat sink connected to the electrode, wherein the heat sink is confined by the electrode and at least a portion of the elongated body.

In accordance with other embodiments, an ablation device includes an electrode, and a heat sink connected to the electrode, wherein the heat sink is not connected to a pump.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention. It should be noted that the figures are not drawn to scale and that elements of similar structures or functions are represented by like reference numerals throughout the figures. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Figure 1:
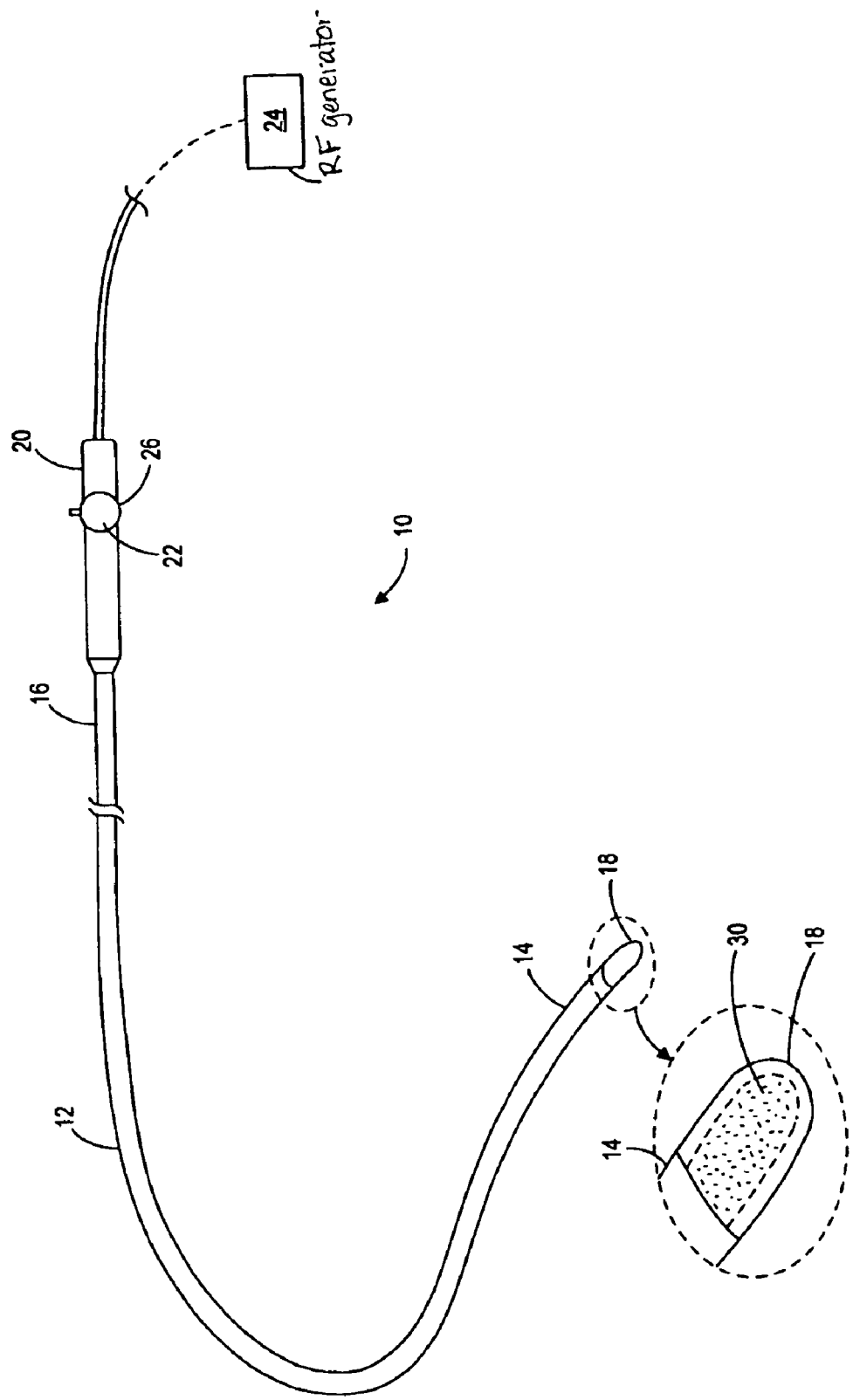
FIG. 1 is an ablation device in accordance with some embodiments.

FIG. 1 illustrates an ablation device 10 in accordance with some embodiments. The ablation device 10 includes an elongated body 12 having a distal end 14 and a proximal end 16, an electrode 18 secured to the distal end 14, and a handle 20 secured to the proximal end 16. During use, the ablation device 10 is connected to a generator 24, so that RF energy can be delivered to the electrode 18. The ablation device 10 also includes a heat sink 30 located within the electrode 18. The heat sink 30 is configured to carry heat away from the electrode 18 during use.

In the illustrated embodiments, the generator 24 is a radio frequency (RF) generator that delivers RF energy to ablate tissue. However, other types of energy, e.g., laser energy, may also be used for tissue ablating purposes. In the illustrated embodiments, the ablation device 10 operates in a unipolar mode. In this arrangement, the generator 24 may include an indifferent patch electrode (not shown) that attaches to the patient's back or other exterior skin area. In this case, ablation energy will flow from the electrode 18 to the patch electrode. Alternatively, the ablation device 10 can be operated in a bipolar mode, in which case, ablation energy will flow from the electrode 18 to an adjacent electrode on the elongated body 12, or vice versa.

The elongated body 12 has a cross-sectional geometry that is circular. However, other cross-sectional shapes, such as elliptical, rectangular, triangular, and various customized shapes, may be used as well. The elongated body 12 may be preformed of an inert, resilient plastic material that retains its shape and does not soften significantly at body temperature, like Pebax®, polyethylene, or Hytrel® (polyester). Alternatively, the elongated body 12 may be made of a variety of materials, including, but not limited to, metals and polymers.

The elongated body 12 is preferably flexible so that it is capable of winding through a tortuous path that leads to a target site, i.e., an area within the heart. Alternatively, the elongated body 12 may be semi-rigid, e.g., by being made of a stiff material, or by being reinforced with a coating or a coil, to limit the amount of flexing. The stiffness or flexibility of the elongated body 12 is a matter of design choice, and will depend on the particular application.

The electrode 18 can be made of a solid, electrically conducting material, such as, e.g., platinum or gold, that is attached to the elongated body 12. Alternatively, the electrode 18 can be formed by coating the distal end 14 of the elongated body 12 with an electrically conducting material, such as, e.g., platinum or gold. The coating can be applied using sputtering, ion beam deposition, or equivalent techniques.

The handle 20 includes a steering mechanism 22 for steering the distal end 14 of the elongated body 12. The steering mechanism 22 includes a rotatable cam 26 and one or more steering wires (not shown) connected between the cam 26 and the electrode 18 (or the distal end 14). During use, the cam 26 can be rotated to apply tension to a steering wire, thereby causing the distal end 14 of the elongated body to bend. Further details regarded the steering mechanism 22 are described in U.S. Pat. No. 5,273,535, the entire disclosure of which is herein incorporated by reference. In other embodiments, the handle 20 does not include the steering mechanism 22.

Figure 2:
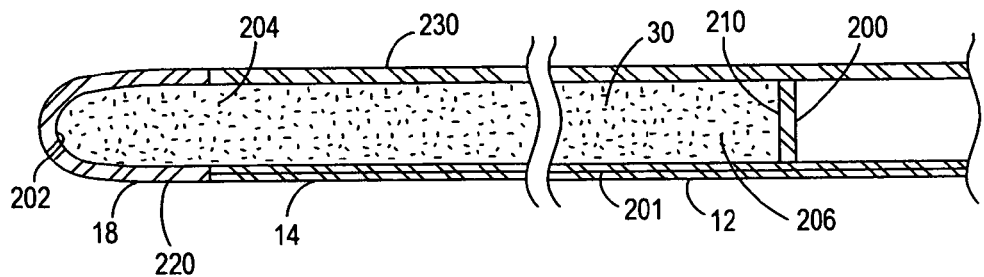
FIG. 2 is a partial cross sectional view of the ablation device of FIG. 1 in accordance with some embodiments.

FIG. 2 illustrates a partial cross section of the ablation device 10 in accordance with some embodiments. As shown in FIG. 2, the electrode 18 has a lumen 202 and is secured to the distal end 14 of the elongated body 12. A wire 201 is provided to deliver energy from the generator 24 to the electrode 18 to energize the electrode 18 during use. The heat sink 30 is confined by the electrode 18 and at least a portion of the elongated body 12. Particularly, the heat sink 30 is located within the lumen 202 of the electrode 12 and a lumen 210 of the elongated body 12. In the illustrated embodiments, the elongated body 12 further includes a wall 200 for confining the heat sink 30. In some embodiments, the wall 200 is located at or adjacent to the distal end 14. In such cases, the heat sink 30 is confined at the distal end of the ablation device 10. Alternatively, the wall 200 can be located at another location along the length of the body 12. For example, the wall 200 can be located at the proximal end 16, in which cases, the heat sink 30 extends from the electrode 18 to the proximal end of the elongated body 12.

The heat sink 30 is configured to carry heat away from the electrode 18, thereby providing a cooling effect for the electrode 18 during use. Cooling causes the electrode-tissue interface to have lower temperature values. As a result, the hottest isothermal region is shifted deeper into the tissue. An electrode that is connected to a heat sink can be used to transmit more ablation energy into the tissue, compared to the same electrode that is not connected to a heat sink.

The heat sink 30 can be made from a variety of materials. In some embodiments, the heat sink 30 can be fluid, such as water, saline, oil, or other chemical agents. The heat sink 30 is preferred to have a boiling point that is higher than 90° C., and more preferably, higher than 100° C. However, in other embodiments, the heat sink 30 can be a fluid having other boiling points. During use, as a distal portion 204 of the heat sink 30 connected to the electrode 18 carries heat away from the electrode 18, fluid at the distal portion 204 of the heat sink 30 is heated. Due to a temperature differential between the distal portion 204 and a proximal portion 206 of the heat sink 30, the heated fluid will move towards the proximal direction, while relatively cool fluid at the proximal portion will move towards the distal direction. Once the heated fluid has traveled away from the electrode 18, it will begin to cool down, and will travel back towards the electrode 18 to carry additional heat away from the electrode 18. As such, fluid of the heat sink 30 will continue to move within the enclosed space due to convection as the heat sink 30 is used to carry heat away from the electrode 18.

In other embodiments, instead of fluid, the heat sink 30 can be made from a solid material, such as ceramic. In such cases, the heat sink 30 can be segmented, or can include a plurality of blocks or particles, thereby allowing the heat sink 30 to change shape when the elongated body 12 is bent. Alternatively, if the elongated body 12 is not intended to be bent during use (e.g., the elongated body 12 is made from a rigid material), the heat sink 30 can be manufactured as a one or more components. The elongated body 12 can be made from a flexible that allows the body 12 to expand as the heat sink 30 undergoes thermal expansion. Alternatively, a gap can be provided between the heat sink 30 and the interior wall of the elongated body 12, thereby allowing the heat sink 30 to undergo thermal expansion without radially expanding the elongated body 12.

In further embodiments, the heat sink 30 can be a gel, such as Alginate. Also, in other embodiments, the heat sink 30 can include a mixture of two or more of fluid (e.g., gas or liquid), solid, and gel.

In some embodiments, the ablation device 10 further includes a container for containing the heat sink 30. In such cases, the container is simply inserted into the lumen 210 of the elongated body 12 during a manufacturing process. The container can be made from a rigid material, or a flexible material (e.g., to form a deformable membrane).

In alternative embodiments, instead of confining the heat sink 30 in the lumen 202 of the electrode 18, the heat sink 30 can be located within a wall 220 of the electrode 18. In such cases, the heat sink 30 is substantially confined within the wall 220 of the electrode 18 and within a side wall 230 of the elongated body 12, and the ablation device 10 does not include the wall 200. Such configuration is beneficial in that the lumen 210 of the elongated body 12 can be used for other functions, such as to house a steering wire, an ablation wire, or other electrical or mechanical components.

Figure 3:
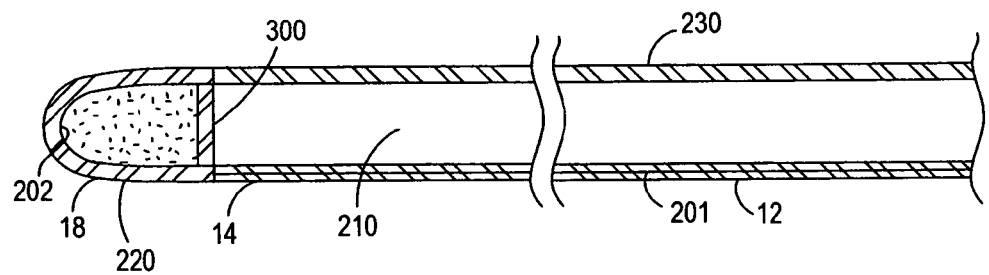
FIG. 3 is a partial cross sectional view of the ablation device of FIG. 1 in accordance with other embodiments.

FIG. 3 illustrates a partial cross section of the ablation device 10 in accordance with other embodiments. As shown in FIG. 3, the lumen 202 of the electrode 18 is enclosed by a wall 300. As such, instead of using a portion of the elongated body 12 to confine the heat sink 30, the heat sink 30 is confined within the lumen 202 of the electrode 18. Such configuration is beneficial in that it allows the heat sink 30 and the electrode 18 to be manufactured as a single component, which can then be secured to the elongated body 12. In the illustrated embodiments, the wall 300 is secured to a proximal end 302 of the electrode 18. The wall 300 can be made from the same material from which the electrode 18 is made, but alternatively, can be made from a different material than that of the electrode 18.

Figure 4:
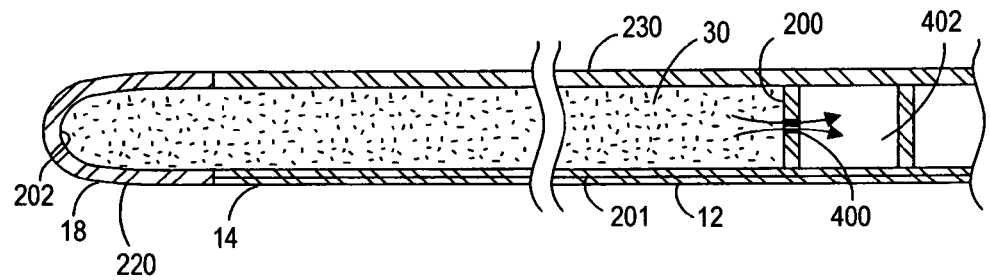
FIG. 4 is a partial cross sectional view of the ablation device of FIG. 1 in accordance with other embodiments.

In the above embodiments, the heat sink 30 is completely confined within the lumen 210 of the elongated body 12 and/or the electrode 18. As such, the heat sink 30 operates in a "closed" system. Such configuration eliminates the need to use a pump and fluid delivery tubing, thereby making it easier for a physician to use. Alternatively, the heat sink 30 can be partially confined, thereby allowing the heat sink 30 to operate in an "open" system. FIG. 4 illustrates a partial cross section of the device 10 in accordance with other embodiments. The device 10 has a similar configuration as that of FIG. 2, except that the wall 200 that is used to confine the heat sink 30 has an opening 400. If the heat sink 30 is made from a fluid or a gel, the opening 400 allows some of the heat sink 30 to exit during use. As shown in FIG. 4, the device 10 can further include a compartment 402 for containing the heat sink 30 that has exited through the opening 400. Alternatively, the compartment 402 can be a tube that is connected to the opening 400. Also, in alternative embodiments, the wall 200 does not include the opening 400. Instead, the wall 230 of the elongated body 12 has an opening (not shown) for allowing some of the heat sink 30 to exit. In such cases, the wall 230 further includes a channel or a lumen for housing or carrying the exited heat sink 30.

Figure 5:
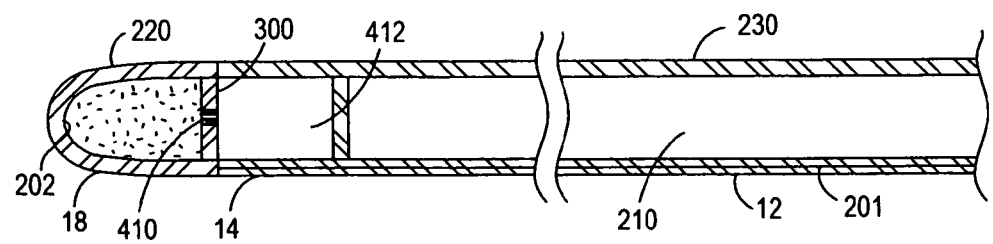
FIG. 5 is a partial cross sectional view of the ablation device of FIG. 1 in accordance with other embodiments.

FIG. 5 illustrates a partial cross section of the device 10 in accordance with other embodiments. The device 10 has a similar configuration as that of FIG. 3, except that the wall 300 that is used to confine the heat sink 30 has an opening 410. If the heat sink 30 is made from a fluid or a gel, the opening 410 allows some of the heat sink 30 to exit during use. As shown in FIG. 5, the device 10 can further include a compartment 412 for containing the heat sink 30 that has exited through the opening 410. Alternatively, the compartment 412 can be a tube that is connected to the opening 410. Also, in alternative embodiments, the wall 300 does not include the opening 410. Instead, the wall 220 of the electrode 18 has an opening (not shown) for allowing some of the heat sink 30 to exit. In such cases, the wall 220 further includes a channel or a lumen for housing or carrying the exited heat sink 30.

Figure 6:
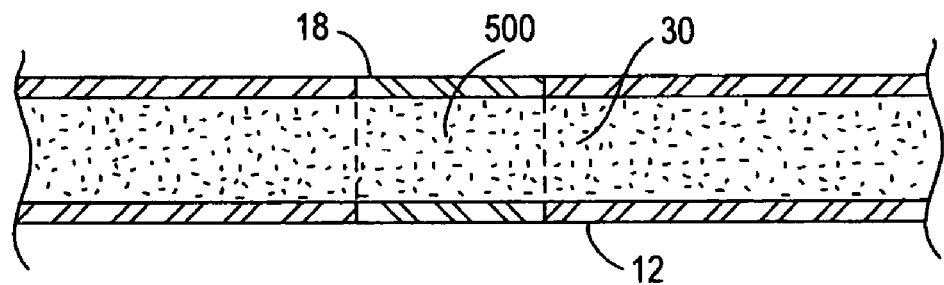
FIG. 6 is a partial cross sectional view of an ablation device having a heat sink employed with a ring electrode in accordance with other embodiments.

In the above embodiments, the electrode 18 is a tip electrode that is secured to the distal end 14 of the elongated body 12. Alternative, the electrode 18 can be secured to the elongated body 12 at a different position. For example, in other embodiments, the electrode 18 can have a ring configuration, and is secured to the elongated body 12 at a point along the length of the elongated body 12 (FIG. 6). As shown in FIG. 6, the heat sink 30 is located within an opening 500 of the ring electrode 18.

Figure 7:
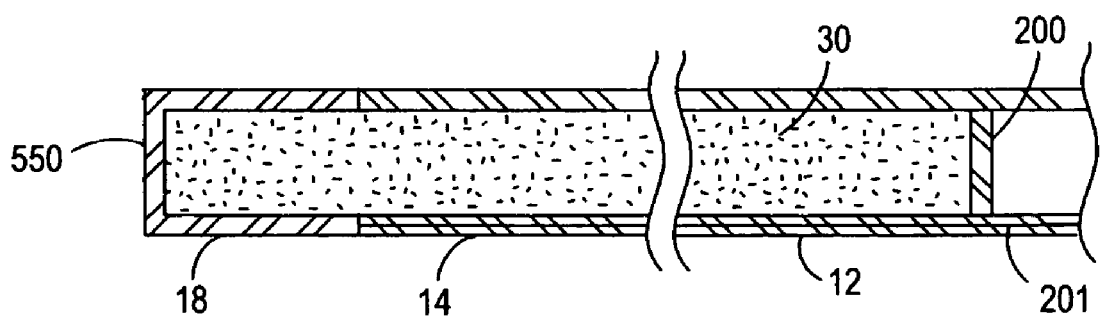
FIG. 7 is a partial cross sectional view of an ablation device having a heat sink employed with an electrode that has a flat distal surface in accordance with other embodiments.

Also, instead of having the shapes illustrated previously, the electrode 18 can have other shapes. For example, the electrode 18 can have a flat surface 550 at a distal tip of the electrode 18 (FIG. 7).

Figure 8:
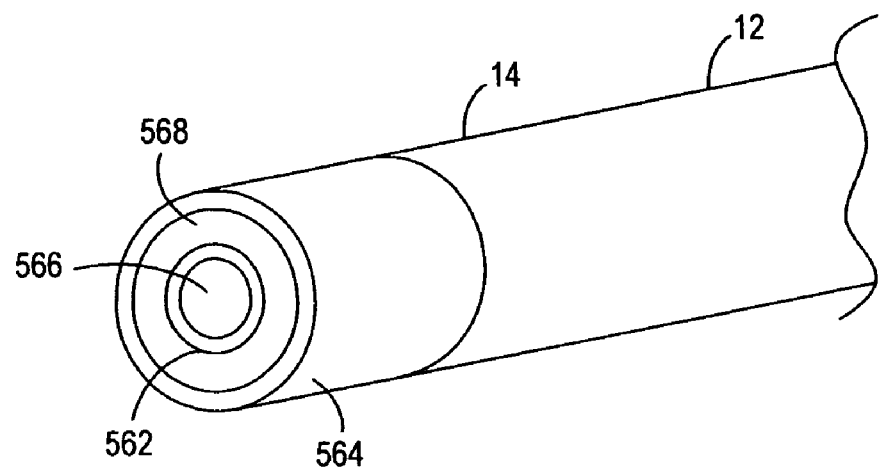
FIG. 8 is a cross-sectional side view of an ablation device having heat sink(s) employed with elongated electrodes in accordance with some embodiments, showing electrodes constrained within a cannula.

In other embodiments, the ablation device 10 can include two electrodes 562, 564 that are positioned relative to each other in a substantially concentric configuration (FIG. 8). In such cases, the heat sink 30 can be located within an opening 566 of the inner electrode 562 and/or the space 568 between the electrodes 562, 564. Double ring electrodes, such as La Placian electrodes, have been described in U.S. patent application Ser. No. 10/318,655, filed on Dec. 12, 2002.

Figure 9:
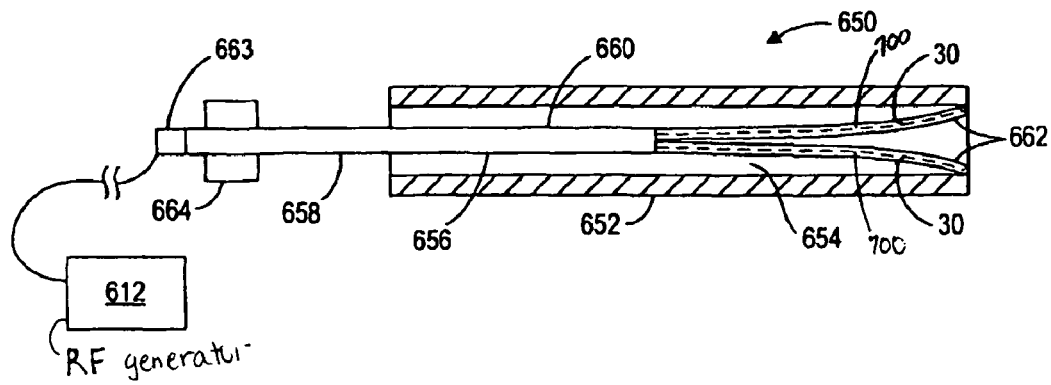
FIG. 9 is a cross-sectional side view of the ablation device of FIG. 8, showing the electrodes deployed from the cannula.
Figure 10:
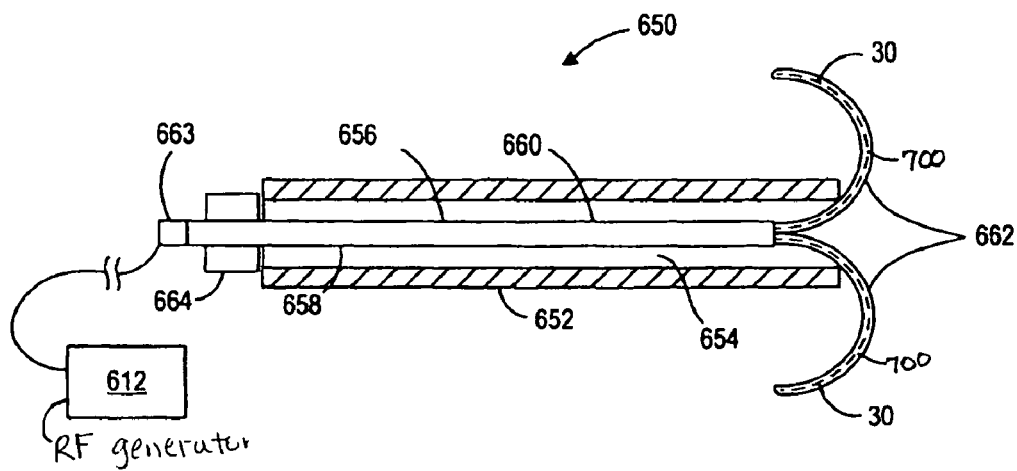
FIG. 10 is a perspective view of an ablation device having heat sink(s) employed with two ring electrodes in accordance with other embodiments.

In other embodiments, the electrode 18 can be a needle electrode that has an elongated shape. FIGS. 9 and 10 illustrate an ablation device 650 having elongated electrodes in accordance with other embodiments. The ablation device 650 includes a cannula 652 having a lumen 654, a shaft 656 having a proximal end 658 and a distal end 660, and a plurality of electrode 662 secured to the distal end 660 of the shaft 656. The proximal end 658 of the shaft 656 may include a connector 663 for coupling to a generator 612.

The cannula 652 coaxially surrounds the shaft 656 such that the shaft 656 may be advanced axially from or retracted axially into the lumen 654 of the cannula 652. Optionally, a handle 664 may be provided on the proximal end 658 of the shaft 656 to facilitate manipulating the shaft 656. The electrodes 662 may be compressed into a low profile when disposed within the lumen 654 of the cannula 652, as shown in FIG. 9. As shown in FIG. 10, the proximal end 658 of the shaft 656 or the handle 664 (if one is provided) may be advanced to deploy the electrodes 662 from the lumen 654 of the cannula 652. When the electrodes 662 are unconfined outside the lumen 654 of the cannula 652, they may assume a relaxed expanded configuration. FIG. 10 shows an exemplary two-electrode array including electrode 662 biased towards a generally "U" shape and substantially uniformly separated from one another about a longitudinal axis of the shaft 656. Alternatively, each electrodes 662 may have another shape, such as a "J" shape, a flared profile, or a rectilinear shape, and/or the array may have one electrode 662 or more than two electrodes 662. The array may also have non-uniform spacing to produce an asymmetrical lesion. The electrode 662 are preferably formed from spring wire, superelastic material, or other material, such as Nitinol, that may retain a shape memory. During use of the ablation device 600, the electrodes 662 may be deployed into a target tissue region to deliver energy to the tissue to create a lesion. Exemplary ablation devices having a spreading array of electrodes have been described in U.S. Pat. No. 5,855,576, the disclosure of which is expressly incorporated by reference herein.

As shown in FIG. 10, the heat sink 30 can be located within a lumen 700 of the electrode 662. In some embodiments, the heat sink 30 located along portion(s) of the electrode 662. Alternatively, the heat sink 30 extends substantially along the length of the electrode 662. In further embodiments, the heat sink 30 can extends to a lumen (not shown) that is located within the shaft 656.

In the above embodiments, the heat sink 30 substantially occupies the space in which it is confined. Alternatively, the heat sink 30 does not substantially occupy the space in which it is confined. For examples, for the case of solid, the heat sink 30 can be sized to occupy only a portion of the lumen 210 within the elongated body 12. In other cases, the heat sink 30 can be coated onto an interior surface of the electrode 18, thereby leaving a substantial portion of the lumen 202 unoccupied by the heat sink 30. Also, in other embodiments, the ablation device 10 can further include an inner tubular member located within the lumen 210 of the elongated body 12. In such cases, the heat sink 30 is located at the space between the inner tubular member and the elongated body 12, and does not occupy the space within the inner tubular member.

Figure 11:
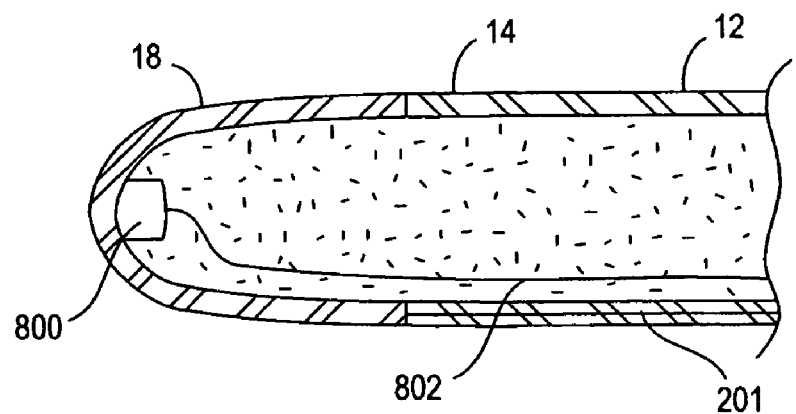
FIG. 11 is a partial cross sectional view of the ablation device of FIG. 1, showing the device having a temperature sensor.

In any of the embodiments described herein, the ablation device can further include a temperature sensor 800 secured to the electrode 18 (FIG. 11). A signal wire 802 can be used to transmit a signal (associated with a temperature of the electrode) to a processor (not shown), which is configured to control an operation of the generator 24 to thereby adjust an amount of energy transmitted to the electrode.

Although the above embodiments have been described with reference to ablation devices, in other embodiments, the heat sink 30 can be employed with other types of medical devices, which may or may not include an electrode.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An ablation device, comprising:
an elongated body having a lumen therein;
an electrode having an enclosed lumen, the electrode secured to a distal end of the elongated body;
a wall disposed in one of the lumen of the elongated body and the lumen of the electrode;
an opening in the wall;
a compartment disposed in the lumen of the elongated body and in direct communication with the opening; and
a fluid heat sink partially confined by the wall and an inner surface of the electrode and configured to operate in an open system wherein the opening allows the heat sink to flow therethrough into the compartment.

2. The ablation device of claim 1, wherein the heat sink comprises a liquid, a gel, or a gas.

3. The ablation device of claim 1, wherein the electrode has a distal end that has a dome shape.

4. The ablation device of claim 1, wherein the electrode has an elongated body.

5. The ablation device of claim 1, wherein the electrode has a ring configuration.

6. The ablation device of claim 1, wherein the electrode has a sharp tip for piercing tissue.

7. The ablation device of claim 1, wherein the opening in the wall is not coupled to a pump.

8. The ablation device of claim 1, wherein the heat sink is not connected to a pump.

9. The ablation device of claim 1, further comprising a temperature sensor secured to the electrode.

10. The ablation device of claim 1, wherein the fluid heat sink is selected from the group consisting of water, saline, and oil.

11. The ablation device of claim 1, wherein the fluid heat sink has a boiling point greater than 90° C.

12. The ablation device of claim 1, wherein the fluid heat sink has a boiling point greater than 100° C.

13. The ablation device of claim 1, wherein the heat sink is moveable between the inner surface of the electrode and the wall in response to heat generated at the electrode.

14. The ablation device of claim 1, wherein a space between the wall and the inner surface of the electrode is sized to contain substantially an entire volume of the fluid heat sink.

15. An ablation device, comprising:
an elongated body having a lumen;
a first wall disposed in the lumen of the elongated body;
a second wall disposed in the lumen of the elongated body and positioned distal to the first wall;
an opening in the second wall;
a first compartment disposed in the lumen of the elongated body and located adjacent to the second wall;
a second compartment disposed in the lumen of the elongated body and located between the first wall and the second wall;
a fluid heat sink occupying substantially the entire first compartment; and
an ablation electrode coupled to a distal end of the elongated body and disposed adjacent to the heat sink.

16. The ablation device of claim 15, wherein the first compartment is formed by the second wall and an inner surface of the ablation electrode.

17. The ablation device of claim 15, wherein the opening in the second wall is configured for allowing the fluid heat sink to flow between the first compartment and the second compartment.

18. The ablation device of claim 15, wherein the fluid heat sink is configured to flow between the first compartment and the second compartment, and wherein the first compartment is sized to contain substantially an entire volume of the fluid heat sink.

19. The ablation device of claim 15, wherein the fluid heat sink has a boiling point greater than 90° C.

20. The ablation device of claim 15, wherein the fluid heat sink has a boiling point greater than 100° C.

21. The ablation device of claim 15, wherein the fluid heat sink is not in communication with a pump.

* * * * *